(12) United States Patent
Shimizu et al.

(10) Patent No.: US 7,033,586 B2
(45) Date of Patent: Apr. 25, 2006

(54) INSECTICIDAL PAECILOMYCES TENUIPES STRAIN FERM BP-7861

(75) Inventors: Susumu Shimizu, Koga (JP); Shinji Isayama, Takarazuka (JP); Eiji Nitta, Nishinomiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 455 days.

(21) Appl. No.: 10/254,657

(22) Filed: Sep. 26, 2002

(65) Prior Publication Data

US 2003/0124098 A1 Jul. 3, 2003

(30) Foreign Application Priority Data

Sep. 26, 2001 (JP) .............................. 2001-293406

(51) Int. Cl.
*A01N 25/00* (2006.01)
*A01N 63/00* (2006.01)
*A01N 63/04* (2006.01)
*A01N 65/00* (2006.01)
*C12N 1/14* (2006.01)

(52) U.S. Cl. .................... 424/93.5; 424/93.1; 424/405; 435/243; 435/254.1; 435/911

(58) Field of Classification Search ................ 435/243, 435/254.1; 424/93.1, 93.5, 405
See application file for complete search history.

(56) References Cited

U.S. PATENT DOCUMENTS 5,360,607 A  11/1994  Eyal et al.

FOREIGN PATENT DOCUMENTS

WO  WO 90/10388 A1  9/1990
WO  WO 95/10597 A1  4/1995

OTHER PUBLICATIONS

T. Fukatsu et al., "Isolation, Inoculation to Insect Host, and Molecular Phylogeny of an Entomogenous Fungus *Paecilomyces tenuipes*", *Journal of Invertebrate Pathology*, vol. 70, Article No. IN974696, 1997, pp. 203-208.

V.G. Zimmerman, "*Paecilomyces tenuipes* (Peck) Samson, ein seltener insektenpathogener Pilz an Noctuiden", *Anzeiger Fur Schadlingskunde Pflanzenschutz Umweltschutz*, vol. 53, XP-008012027, 1980, pp. 69-72.

J.D. Harper, "*Paecilomyces Tenuipes*—in vitro Culture and Host Infectivity Studies", *Stichting Fourth International Colloquium on Invertebrate Pathology*, XP-008012026, Aug. 1986, p. 247.

Database BIOSIS 'Online! Biosciences Information Service, Philadelphia, PA, US; 1995 Sung Jae-Mo et al., "Classification of Cordyceps spp. By morphological characteristics and protein banding pattern", Database accession No. PREV199598418738, XP-002226469.

R.A. Samson, "Paecilomyces and Some Allied Hyphomycetes ", *Studies in Mycology*, No. 6, XP-008012029, 1974, pp. 1-119.

M. Obornik et al., "Phylogeny of mitosporic entomopathogenic fungi: Is the genus *Paecilomyces* polyphyletic?", *Canadian Journal of Microbiology*, vol. 47, No. 9, Sep. 11, 2001, pp. 813-819.

A. Kana-Uchi et al., "Light-induced fruit body formation of an entomogenous fungus *Paecilomyces tenuipes*", *Mycoscience*, vol. 40, 1999, pp. 349-351.

V. Zimmermann, "*Paecilomyces tenuipes* (Peck) Samson, a rarely occurring entomopathogenic fungus attacking noctuids", Anz. Schädlingskde., Pflanzenschutz, Umweltschutz 53, 1980, pp. 69-72, with English Abstract.

T. Fukatsu et al., "Isolation, Inoculation to Insect Host, and Molecular Phylogeny of an Entomogenous Fungus *Paecilomyces tenuipes*", *Journal of Invertebrate Pathology*, vol. 70, 1997, pp. 203-208.

K. Yamanaka et al., "Cultivation characteristics of *Isaria japonica*", *Mycoscience*, vol. 39, 1998, pp. 43-48.

*Primary Examiner*—David M. Naff
*Assistant Examiner*—Deborah K. Ware
(74) *Attorney, Agent, or Firm*—Sughrue Mion, PLLC

(57) ABSTRACT

The present invention provides a *Paecilomyces tenuipes* T1 FERM BP-7861, insecticidal compositions, methods and uses. The insecticidal compositions comprise an insecticidally effective amount of *Paecilomyces tenuipes* T1 FERM BP-7861. The methods comprise applying *Paecilomyces tenuipes* T1 FERM BP-7861 to at least one location selected from a pest, a habitat of the pest and a plant. The uses are uses of *Paecilomyces tenuipes* T1 FERM BP-7861 for controlling a pest.

8 Claims, No Drawings

SEQUENCE LISTING

<160> NUMBER OF SEQ ID NOS: 2

<210> SEQ ID NO 1
<211> LENGTH: 156
<212> TYPE: DNA
<213> ORGANISM: Paecilomyces tenuipes

<400> SEQUENCE: 1
aactttcaac aacggatctc ttggttctgg catcgatgaa gaacgcagcg aaatgcgata    60
cgtaatgtga attgcagaat tccgtgaatc atcgaatctt tgaacgcaca ttgcgcccgc   120

-continued

```
cagcattctg gcgggcatgc ctgttcgagc gtcatt                              156

<210> SEQ ID NO 2
<211> LENGTH: 561
<212> TYPE: DNA
<213> ORGANISM: Paecilomyces tenuipes

<400> SEQUENCE: 2
aaaccaacag ggattgcccc agtaacggcg agtgaagcgg caacagctca aatttgaaat      60
ctggcccccg ggtccgagtt gtaatttgca gaggatgctt cgggcgaggt gccttccgag    120
ttccctggaa cgggacgcca cagagggtga gagcccccgtc tggtcggaca ccgagcccgt   180
gtgaagctcc ttcgaagagt cgagtagttt gggaatgctg ctcaaaacgg gaggtatatg    240
tcttctaaag ctaaatattg gccagagacc gatagcgcac aagtagagtg atcgaaagat    300
gaaaagcact ttgaaaagag ggttaaaaag tacgtgaaat tgttgaaagg gaagcgccca    360
tgaccagact tgggcccggt gaatcacccg gcgttctcgc cggtgcactt tgccgggcac    420
aggccagcat cagtttggcg cgggggagaa aggcttcggg aacgtggctc cctcgggagt    480
gttatagccc gctgcgcaat accctgcgcc ggactgaggt acgcgcatcg caaggatgct    540
ggcgtaatgg tcatcagcga c                                              561
```

INSECTICIDAL PAECILOMYCES TENUIPES STRAIN FERM BP-7861

TECHNICAL FIELD

The present invention relates to a fungus which is insecticidally entomopathogenic to insect pests and which is categorized under the genus *Paecilomyces*.

BACKGROUND ART

In the art of insecticidal compositions, there has been developed insecticidal compositions which utilize therein synthetic insecticidal compounds and insecticidal compositions which have as its origin a microorganism.

Several searches have been conducted heretofore for an entomopathogenic fungus to anticlimactically provide an entomopathogenic filamentous fungus having an insufficient insecticidal effect. Typically, such known entomopathogenic fungi have provided a narrow insecticidal spectrum.

SUMMARY OF THE INVENTION

The present invention provides a biologically pure culture of *Paecilomyces tenuipes* T1 FERM BP-7861, insecticidal compositions, methods and uses. The insecticidal compositions comprise an insecticidally effective amount of *Paecilomyces tenuipes* T1 FERM BP-7861. The methods comprise applying *Paecilomyces tenuipes* T1 FERM BP-7861 to at least one location selected from an insect pest, a habitat of the insect pest and a plant vulnerable to the insect pest. The uses are uses of *Paecilomyces tenuipes* T1 FERM BP-7861 for controlling an insect pest.

DETAILED DESCRIPTION OF THE INVENTION

First, the taxonoomical properties of *Paecilomyces tenuipes* T1 FERM BP-7861 are described below.

(1) the growth rate (25° C., 7 days) diameter of the colony: 25~30 mm (2% maltose extract agar medium plate), 25~30 mm (oatmeal agar medium plate)

(2) color of the front surface of colony white (2% maltose extract agar medium plate), white (oatmeal agar medium plate)

(3) color of the undersurface of colony white (2% maltose extract agar medium plate), white to light yellow (oatmeal agar medium plate)

(4) texture of the front surface of colony wool-like to down-like (5) conidiophore smooth-surfaced branching and unstructured verticil (6) conidium smooth-surfaced elliptical to circular shape linkage, about 4 μm×about 2 μm (7) chlamydospore none (25° C., 9 day period)

(8) nucleotide sequence of DNA coding 5.8S ribosomal RNA of nucleus and nucleotide sequence of DNA coding 28S ribosomal RNA of nucleus the nucleotide sequence of the DNA encoding the 5.8S ribosomal RNA of the nucleus is shown in SEQ ID NO: 1 and the nucleotide sequence of the DNA encoding the 28S ribosomal PNA of the nucleus is shown in SEQ ID NO: 2.

Searches in the Entomopathogenic Fungi Database with a homology search with the nucleotide sequence of DNA coding 5.8S ribosomal RNA of nucleus and the nucleotide sequence of DNA coding 28S ribosomal RNA of nucleus (utilized database: Genbank, utilized program: BLAST (Basic Local Alignment Search tool)(National Center for Biotechnology Information)) show that *Paecilomyces tenuipes* T1 FERM BP-7861 is categorized under *Paecilomyces tenuipes* species.

*Paecilomyces tenuipes* T1 FERM BP-7861 has been deposited with the National Institute of Advanced Industrial Science and Technology International Patent Organism Depository and has been assigned FERM BP-7861 as an accession number.

Next, the present invention insecticidal compositions are described.

The present invention insecticidal compositions comprise an insecticidally effective amount of *Paecilomyces tenuipes* T1 FERM BP-7861. In the present invention insecticidal compositions, living fungus cells of *Paecilomyces tenuipes* T1 FERM BP-7861 are typically present therein. As a living fungus cell of *Paecilomyces tenuipes* T1 FERM BP-7861, for example, there is mentioned a conidium thereof, a blastospore thereof and a hypha thereof The present invention insecticidal compositions can utilize the conidium, blastospore and hypha independently or in mixture.

*Paecilomyces tenuipes* T1 FERM BP-7861 can be prepared, as well as in large amounts, by culturing *Paecilomyces tenuipes* T1 FERM BP-7861 in a liquid culture medium or a solid culture medium.

The culture medium utilized in culturing *Paecilomyces tenuipes* T1 FERM BP-7861 is not limited if the culture medium allows *Paecilomyces tenuipes* T1 FERM BP-7861 to proliferate. For example, there can be utilized culture mediums which are conventionally utilized with culturing microorganisms. Such conventional culture mediums contain appropriately a carbon source, nitrogen source and a salt (such as an organic salt or an inorganic salt). Typically, such conventional culture mediums are liquid culture mediums or solid culture mediums.

The liquid culture medium can be usually prepared by appropriately mixing water with the carbon source, the nitrogen source, the salt and so on.

As the carbon source contained in the liquid culture medium, for example, there is mentioned sugars such as glucose, dextrin and sucrose; sugar alcohols such as glycerol; organic acids such as fumaric acid, citric acid and pyruvic acid; animal oils; plant oils; molasses and the like. The amount of the carbon source contained in the culture medium is usually 0.1 to 20% (w/v).

As the nitrogen source contained in the liquid culture medium, for example, there is mentioned natural organic nitrogen sources such as meat extract, peptone, yeast extract, malt extract, soybean powder, corn steep liquor, cotton seed powder, dried yeast and casamino acid; ammonium salts or nitrates of inorganic acids such as sodium nitrate, ammonium chloride, sodium sulfate and ammonium phosphate; ammonium salts of organic acids such as ammonium fumarate and ammonium citrate; urea; amino acids and the like. The amount of the nitrogen source contained in the liquid culture medium is usually 0.1 to 30% (w/v).

As the organic salt or inorganic salt contained in the liquid culture medium, for example, there is mentioned chlorides, sulfates, nitrates, acetates, carboxylates or phosphates of potassium, sodium, magnesium, calcium, iron, manganese, cobalt, zinc and the like. More specifically, for example, there is mentioned sodium chloride, potassium chloride, magnesium sulfate, iron (I) sulfate, manganese sulfate, cobalt chloride, zinc sulfate, copper sulfate, sodium acetate, calcium carboxylate, sodium carboxylate, potassium phosphate monohydrate, potassium phosphate dihydrate and the like. The amount of the inorganic salt or organic salt contained in the culture medium is usually 0.0001 to 5% (w/v).

As more specific examples of the liquid culture medium utilized to culture *Paecilomyces tenuipes* T1 FERM BP-7861, there is mentioned 2% maltose extract liquid medium, oatmeal liquid medium, potato dextrose liquid medium, Sabouraud liquid medium, L-broth liquid medium and the like.

As the solid culture medium, for example, there is mentioned crops such as rice, wheat, maize, millet, barnyard grass, kaoliang and buckwheat and mixtures thereof; those which contains as a main ingredient sawdust, bagasse, rice hulls, peas, straw, corn cob or cotton seed lees, with as needed, rice bran, corn bran, corn steep liquor, yeast powder, wheat bran, amino acids, soy meal, flour, tofu refuse, glucose, maltose extract, mineral (potassium (I) phosphate, carbonated coal, calcium sulfate, magnesium sulfate and the like) or vitamin (such as thiamin); those which contain as a carrier, a porous material such as clay minerals or naturally-occurring macromolecules such as agar and gelatin, with the carbon source, the nitrogen source or the salt which are utilized for the above cited liquid culture mediums and the like.

As more specific examples of the solid culture medium utilized to culture *Paecilomyces tenuipes* T1 FERM BP-7861, there is mentioned 2% maltose extract agar medium, oatmeal agar medium, potato dextrose agar medium, Sabouraud agar medium, L-broth agar medium and the like.

The culturing of *Paecilomyces tenuipes* T1 FERM BP-7861 can be conducted accordingly to methods conventionally utilized to culture microorganisms.

As methods which culture with the liquid medium, for example, there is mentioned test tube shake culture, reciprocal culture, jar fermenter, tank culture and the like.

As methods which culture with the solid medium, for example, there is mentioned stationary culture.

The conditions for culturing *Paecilomyces tenuipes* T1 FERM BP-7861 with the liquid or solid culture medium are as follows. The culture temperature can appropriately change in a range which allows a microorganism to grow, but is typically a range of about 15 to 35° C. The pH of the liquid or solid culture medium is usually the range of about 5 to 7. The culture time way change with the culturing conditions, but is usually in the range of about 1 day to about 2 months.

After culturing with the liquid culture medium, *Paecilomyces tenuipes* T1 FERM BP-7861 can be obtained by a method in which the liquid culture medium that cultured *Paecilomyces tenuipes* T1 FERM BP-7861 is centrifuged. After culturing with the solid culturing medium, *Paecilomyces tenuipes* T1 FERM BP-7861 can be obtained by a method in which distilled water is added onto the solid culture medium that cultured *Paecilomyces tenuipes* T1 FERM BP-7861 and which *Paecilomyces tenuipes* T1 FERM BP-7861 is scraped from the surface thereof.

The present invention insecticidal compositions can utilize *Paecilomyces tenuipes* T1 FERM BP-7861 independently, but may further utilize therein a solid carrier, liquid carrier or the like to formulate *Paecilomyces tenuipes* T1 FERM BP-7861. As needed, the present invention insecticidal compositions may have added thereto a formulation adjuvant such as a surfactant, water retention agent and the like.

In such cases of formulation, the present invention insecticidal compositions can be formulated as a solid formulation such as a granule, dust and wettable powder or as a liquid formulation such as an emulsifiable concentrate, flowable, oily formulation and the like.

In such formulations, *Paecilomyces tenuipes* T1 FERM BP-7861 is typically present therein at an amount of about $10^3$ to $10^{15}$ CFU (CFU: colony forming unit), for 1 g of the present invention insecticidal compositions.

As the solid carrier utilized when formulating, for example, there is mentioned clays such as serite, kaolin clay, diatomaceous earth, synthetic hydrated silicon oxide, bentonite, Fubasami clay and acid clay; tales; ceramics; other inorganic minerals; organic materials such as peat moss, pulp, agar and bran and the like.

As the liquid carrier, there is mentioned water, aliphatic hydrocarbons such as hexane, kerosene and light oil; horticultural oils such as machine oil; plant oils such as soy oil and cotton seed oil and the like.

As the surfactant for example, there is mentioned alkylsulfuric acid esters; alkylsulfonic acid salts; alkyl aryl sulfonic acid salts; alkyl aryl ethers; polyoxyethylenealkyl ethers of alkyl aryl ethers; polyoxyethylenealkyl esters of alkyl aryl ethers; polyoxyethylenealkylphenyl ethers; polyoxycthylencalkylphenyl esters; polyoxyetylene fatty acid esters; polyoxyethylenesorbitan fatty acid esters; polyethyleneglycol ethers; polyhydric alcohol esters; sugar alcohols and the like.

As the water retention agent, for example, there is mentioned adhesive sugars such as carrageenan, Zanthan gum, sodium alginic acid, carboxyrmethylcellulose and sodium hydroxyethylcellulose; adhesive synthetic water soluble polymers such as sodium polyacrylic acid, polyethyleneimine, polyvinyl alcohol, polyethylene oxide and polyvinyl pyrolidone; adhesive animal polymers such as sodium chondroitin sulfuric acid, casein and gelatin; polyhydric alcohol such as glycerin and ethyleneglycol and the like.

As insect pests to which *Paecilomyces tenuipes* T1 FERM BP-7861 has an effect, for example, there is mentioned the following insect pests. Lepidoptera: Pyralidae such as rice stem borer (*Chilo suppressahis*), rice leaf roller (*Cnaphalocrocis medinalis*); Noctuidae such as cabbage armyworm (*Mamestra brasicae*), corn earworm (*Helicoverpa armigera*), beet semi-looper (*Autographa nigrisigna*); whites (Pierdae) such as common cabbageworm (*Pieris rapae*); yponomeutids (Yponomeutidae) such as diamondback moth (*Plutella xylostella*); tussock moths (Lymantriidae) such as *Euproctis taiwana*, gypsy moth (*Lymantria dispar*), browntail moth (*Euproctis similis*); slug caterpillar moths (Limacodidae) such as oriental moth (*Scopelodes contracus*); tent caterpillar moths (Lasiocampidae) such as pine caterpillar (*Dendrolimus spectabilis*) and the like Hemiptera: aphids (Aphididae) such as cotton aphid (*Aphis gossypii*), green peach aphid (*Myzus persicae*) and turnip aphid (*Lipaphis pserudobrassicae*); whiteflies (Aleyrodidae) such as greenhouse whitefly (*Trialeurodes vaporariorum*), sweetpotato whitefly (*Bemisia tabact*), *Beemisia argentifolli* and the like Diptera: muscid flies (Muscidae) such as housefly (*Musca domestics*); mosquitoes (Culicidae) such as common mosquito (*Culex pipiens pallens*) and the like Thripidae: *Thrips palmi*, western flower thrips (*Frankliniella occidentalis*) and the like Isoptera: *Reticulitermes speratus*, Formosan subterranean termite (*Coptotermes formosanus*) and the like The present invention insecticidal method is typically conducted by applying an insecticidally effective amount of the present invention insecticidal composition to a location selected from the insect pest, a habitat of the insect pest or to a plant vulnerable to the insect pest. For example, the present invention insecticidal compositions may be applied to a crop, in order to be protected from the insect pest.

When applying the present invention insecticidal composition, the application amount thereof is usually for 1000 m$^2$, $10^5$ to $10^{19}$ CFU, preferably $10^7$ to $10^{17}$ CFU. The emulsifiable concentrate, wettable powder and the flowable is typically diluted so that the concentration of the present invention fungus body is $10^3$ to $10^{12}$ CFU/ml and the granule is usually applied directly.

The present invention insecticidal compositions can be utilized by foliage applying a present invention insecticidal composition to a plant vulnerable to an insect pest, in order to protect The plant from the insect pest. Further, the present invention insecticidal compositions can also be utilized by applying the present invention insecticidal compositions to the seedbed before planting or to the plant foot after planting said plant.

EXAMPLES

The present invention is described in further detail by the following examples, but the present invention is not limited to these examples.

Production Example

*Paecilomyces tenuipes* T1 FERM BP-7861, which was previously cultured in potato dextrose agar medium, was inoculated to potato dextrose agar medium (diameter 90 mm×depth 10 mm). The *Paecilomyces tenuipes* FERM BP-7861 was then cultured under stationary culture methods for 14 days while being exposed to a fluoresent lamp at 14 hours/day at 25° C. The fungus cells formed on the agar medium (including many conidium) were gathered by scraping with 10 ml of solution in which 0.03% spreader (Lino, Nihon Nohyaku Co.) is dissolved in distilled water. The resulting solution was diluted further with the 0.03% spreader to prepare a test liquid of *Paecilomyces tenuipes* T1 FERM BP-7861.

Reference Example

Each of *Paecilomyces tenuipes* ATCC-44818, *Isaria japonica* IFO 30367 and *Isaria japonica* IFO-31161 was prepared as a test liquid similar to the above Production Example.

*Isaria japonica* has been categorically included under the species of *Paecilomyces tenuipes* (for example, "Plant Protection" a special issue No.2, Manual for the Researches on Insect Pathoges, published by Japan Plant Protection Association).

Test Example 1

In a plastic cup of a diameter of 6 cm and a height of 3 cm, filter paper of a diameter of 5 cm was added thereto. Subsequently, 0.6 ml of the test liquid of *Paecilomyces tenuipes* T1 FERM BP-7861 was added. After 0.5 g of sucrose and 10 adult houseflies were added to the cup, the opening of the cup was closed. After 4 days, the number of dead and alive insect pests was observed and the mortality was determined (3 repetitions)

Further, as comparative examples, the test liquids prepared with the method described in the Reference Example were used in a similar manner to observe the number of dead and alive insect pests thereof and to determine the mortality thereof.

The results are shown in Table 1.

TABLE 1

| Tested fungus strain | concentration of fungus cells (CFU/ml) | mortality (%) |
|---|---|---|
| *Paecilomyces tenuipes* T1 FERM BP-7861 | $1 \times 10^8$ | 97 |
| *Paecilomyces tenuipes* ATCC-44818 | $1 \times 10^8$ | 10 |
| *Isaria japonica* IFO30367 | $1 \times 10^8$ | 0 |
| *Isaria japonica* IFO-31161 | $3 \times 10^8$ | 3 |
| untreated (0.03% spreader) | | 0 |

Test Example 2

Cabbages were planted in plastic cups and were allowed to grow for 3 weeks. The test liquid of *Paecilomyces tenuipes* T1 FERM BP-7861 was sprayed (10 ml/pot) to the cabbages. After allowing the cabbages to dry, 10 diamondback moth larvae at the 3rd instar stage were released onto each of the cabbages. After 5 days, the number of dead and alive insect pests was observed and the mortality was determined (3 repetitions).

Further, as comparative examples, the test liquids prepared with the method described in the Reference Example were used in a similar manner to observe the number of dead and alive insect pests thereof and to determine the mortality thereof The results are shown in Table 2.

TABLE 2

| Tested fungus strain | concentration of fungus cells (CFU/ml) | mortality (%) |
|---|---|---|
| *Paecilomyces tenuipes* T1 FERM BP-7861 | $1 \times 10^7$ | 74 |
| *Paecilomyces tenuipes* ATCC-44818 | $3 \times 10^7$ | 40 |
| *Isaria japonica* IFO30367 | $1 \times 10^7$ | 10 |
| *Isaria japonica* IFO-31161 | $5 \times 10^7$ | 14 |
| untreated (0.03% spreader) | | 0 |

Test Example 3

For 10 seconds, corn earworm larvae at the 3rd instar stage were dipped in the test liquid of *Paecilomyces tenuipes* T1 FERM BP-7861 prepared according to the method described in Production Example 1. In plastic cups of a diameter of 6 cm and a height of 3 cm, filter papers of a diameter of 5 cm were added thereto. Subsequently, 1 of the above test insect pests and a cabbage leaf were added thereto, respectively. The opening to the cup was then closed. After 7 days, the number of dead and alive insect pests was observed and the mortality was determined (10 repetitions).

Further, as comparative examples, the test liquids prepared with the method described in the Reference Example were used in a similar manner to observe the number of dead and alive insect pests thereof and to determine the mortality rate thereof.

The results are shown in Table 3.

TABLE 3

| Tested fungus strain | concentration of fungus cells (CFU/ml) | mortality (%) |
|---|---|---|
| *Paecilomyces tenuipes* T1 FERM BP-7861 | $1 \times 10^7$ | 80 |
| *Paecilomyoes tenuipes* ATCC-44818 | $3 \times 10^7$ | 60 |
| *Isaria japonica* IFO30367 | $1 \times 10^7$ | 0 |
| *Isaris japonica* IFO-31161 | $7 \times 10^7$ | 10 |
| untreated (0.03% spreader) | | 0 |

Test Example 4

Cucumbers were planted in plastic cups. After allowing the cucumbers to grow for 2 weeks, 5 female adult cotton aphids were released per pot. To these cucumbers, 10 ml per pot of the test liquid of *Paecilomyces tenuipes* T1 FERM BP-7861 was sprayed. After 8 days, the number of dead and alive insect pests was observed and the corrected population density index was determined with the following equation.

Further, as comparative examples, the test liquids prepared with the method described in the Reference Example were used in a similar manner to observe the number of dead and alive insect pests thereof and to determine the mortality thereof.

$$\text{corrected population density index} = \{(A \times b)/(B \times a)\} \times 100$$

A: number of living insect pests in the untreated before application
a: number of living insect pests in the untreated 8 days after application
B: number of living insect pests in the treated before application
b: number of living insect pests in the treated 8 days after application The results are shown in Table 4.

TABLE 4

| Tested fungus strain | concentration of fungus cells (CFU/ml) | corrected population density index |
|---|---|---|
| *Paecilomyces tenuipes* T1 FERM BP-7861 | $1 \times 10^7$ | 2 |
| *Paecilomyces tenuipes* ATCC-44818 | $3 \times 10^7$ | 43 |
| *Isaria japonica* IFO30367 | $1 \times 10^7$ | 35 |
| *Isaria japonica* IFO-31161 | $5 \times 10^7$ | 76 |
| untreated (0.03% spreader) | | 100 |

Test Example 5

For 10 seconds, 10 Formosan subterranean termites were dipped in 1.5 ml of the test liquid of *Paecilomyces tenuipes* T1 FERM BP-7861 prepared according to the method described in Production Example 1. The Formosan subterranean termites with the test liquid were poured into a circular petri dish (diameter 90 mm, height 15 mm) having a filter paper of diameter 82 mm placed therein. After 7 days, the number of dead and alive insect pests was observed and the mortality was determined (3 repetitions).

Further, as comparative examples, the test liquids prepared with the method described in the Reference Example were used in a similar manner to observe the number of dead and alive insect pests thereof and to determine the mortality rate thereof.

The results are shown in Table 5.

TABLE 5

| Tested fungus strain | concentration of fungus cells (CFU/ml) | mortality (%) |
|---|---|---|
| *Paecilomyces tenuipes* T1 FERM BP-7861 | $1 \times 10^8$ | 100 |
| *Paecilomyces tenuipes* ATCC-44818 | $1 \times 10^8$ | 3 |
| *Isaria japonica* IFO30367 | $1 \times 10^8$ | 0 |
| *Isaria japonica* IFO-31161 | $3 \times 10^8$ | 6 |
| untreated (0.03% spreader) | | 0 |

The above results in Test Examples 1 to 5 evidence that *Paecilomyces tenuipes* T1 FERM BP-7861 provides an excellent insecticidal effect and that *Paecilomyces tenuipes* T1 FERM BP-7861 has a broad insecticidal spectrum.

What is claimed is:

1. A biologically pure *Paecilomyces tenuipes* strain FERM BP-7861.

2. A composition comprising an insecticidally effective amount of *Paecilomyces tenuipes* strain FERM BP-7861 and a carrier.

3. A method comprising applying an insecticidally effective amount of *Paecilomyces tenuipes* strain FERM BP-7861 to at least one location selected from an insect pest, a habitat of the insect pest and a plant vulnerable to the insect pest.

4. The method according to claim 3, wherein the insect pest is a Lepidopteran pest.

5. The method according to claim 3, wherein the insect pest is a Hemipteran pest.

6. The method according to claim 3, wherein the insect pest is a Dipteran pest.

7. The method according to claim 3, wherein the insect pest is a Thripidae pest.

8. The method according to claim 3, wherein the insect pest is an Isopteran pest.

* * * * *